(12) United States Patent
Lindström

(10) Patent No.: US 6,773,493 B2
(45) Date of Patent: Aug. 10, 2004

(54) WATER SEPARATOR FOR A GAS ANALYZER

(75) Inventor: Christoph Lindström, Örsundsbro (SE)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 10/255,794

(22) Filed: Sep. 26, 2002

(65) Prior Publication Data

US 2003/0066428 A1 Apr. 10, 2003

(30) Foreign Application Priority Data

Oct. 8, 2001 (EP) .......................................... 01000523

(51) Int. Cl.$^7$ .......................................... B01D 35/02
(52) U.S. Cl. ........................ 96/413; 55/422; 73/863.23; 422/88
(58) Field of Search ............................. 55/422, 385.1, 55/528; 96/413; 73/863.23; 422/88; 128/205.29

(56) References Cited

U.S. PATENT DOCUMENTS

| | | | |
|---|---|---|---|
| 2,702,089 A | | 2/1955 | Engelder ..................... 96/118 |
| 4,152,923 A | * | 5/1979 | Courbon ..................... 73/28.04 |
| 4,155,247 A | * | 5/1979 | Kaczmarek et al. ..... 73/863.23 |
| 4,461,183 A | * | 7/1984 | Wedding ................. 73/863.21 |
| 4,796,475 A | * | 1/1989 | Marple ..................... 73/863.22 |
| 4,886,528 A | | 12/1989 | Aaltonen et al. ................. 96/6 |
| 4,961,916 A | * | 10/1990 | Lesage et al. ................. 422/88 |
| 4,963,167 A | * | 10/1990 | Young ......................... 95/273 |
| 5,054,328 A | * | 10/1991 | Long et al. .............. 73/864.81 |
| 5,306,420 A | * | 4/1994 | Bisconte ..................... 210/143 |
| 5,308,483 A | * | 5/1994 | Sklar et al. ................. 210/232 |
| 5,800,597 A | * | 9/1998 | Perrotta et al. ................... 96/9 |
| 6,550,347 B2 | * | 4/2003 | Bradley .................... 73/863.21 |
| 2003/0075049 A1 | * | 4/2003 | Larsen et al. ..................... 96/4 |

FOREIGN PATENT DOCUMENTS

| | | |
|---|---|---|
| DE | 38 44 456 | 7/1989 |
| DE | 41 01 194 | 8/1992 |
| WO | 00/45884 | 8/2000 |

* cited by examiner

Primary Examiner—Richard L. Chiesa
(74) Attorney, Agent, or Firm—Andrus, Sceales, Starke & Sawall, LLP

(57) ABSTRACT

A water separator for a gas analyzer, comprising a housing, a first chamber disposed within the housing, a second chamber disposed within the housing, a first wall formed of a gas permeable and liquid impermeable material separating the chambers, means for introducing a gas sample containing a liquid into the first chamber with a first portion of gas passing through the first wall to the second chamber and a second portion of the gas and the liquid remaining in the first chamber, means for flowing said first portion of the gas from the second chamber to a measuring unit, a water receiving means mounted in the housing, and connected to the first chamber for receiving the second portion of the gas and for separating liquid from the second portion of the gas, a third chamber connected to the water receiving means, a fourth chamber, a second wall formed of a gas permeable and liquid impermeable material separating the third and fourth chambers, the second portion of the gas passing through the second wall to the fourth chamber, and discharge means for discharging the second portion of the gas from the fourth chamber and connecting the water receiving means with a source of vacuum. At least a part of the third chamber is formed to extend over essentially about 360 degrees around a cross sectional area of the housing.

20 Claims, 6 Drawing Sheets

WATER SEPARATOR FOR A GAS ANALYZER

CROSS REFERENCE TO RELATED APPLICATION

The present application claims priority from European Patent Application No. 01000523.9, filed Oct. 8, 2001.

The invention relates to a water separator for a gas analyzer, comprising a housing, a first chamber disposed within the housing, a second chamber disposed within the housing, a first wall formed of a gas permeable and liquid impermeable material separating the chambers, means for introducing a gas sample containing a liquid into the first chamber with a first portion of gas passing through the first wall to the second chamber and a second portion of the gas and the liquid remaining in the first chamber, means for flowing said first portion of the gas from the second chamber to a measuring unit, a water receiving means mounted in the housing, and connected to the first chamber for receiving the second portion of the gas and for separating liquid from the second portion of the gas, a third chamber connected to the water receiving means, a fourth chamber, a second wall formed of a gas permeable and liquid is impermeable material separating the third and fourth chambers, the second portion of the gas passing through the second wall to the fourth chamber, and discharge means for discharging the second portion of the gas from the fourth chamber and connecting the water receiving means with a source of vacuum.

For example, when using a CO2 analyzer for measuring alveolar air, a problem encountered is the vapour contained in exhalation air. Since temperature in a sampling passage is lower than the human body temperature, the water vapour condensates in a measuring device and the intrusion of water drops inside a measuring sensor results in the failure of a measurement. In addition, a gas sample often entraps mucus and blood as well as dust which the water separator must also be capable of removing from gas.

In prior known gas analyzers, water has been removed from a gas sample by using a water separator, provided with a water-separation chamber which divides the flow into two partial flows in a manner that the main flow is sucked through a measuring sensor by means of a tube connected with the water-separation chamber and the many times lesser side flow is sucked continuously by way of a tube connected with the bottom section of said water-separation chamber into a water receiver for retaining therein the water contained in a gas sample and further on to a pump.

It has also been known in the art to use a moisture-equalizing tube. In this case, the analyzer is not usually fitted with individual water-separator but, instead, a sampling tube between a patient and the apparatus as well as a tube between a sampling connector in the apparatus and a measuring sensor are made of a material which equalizes moisture of the gas inside the tube to be the same as that on the outside, so that water always tends to find its way towards the drier side, the moisture of a gas sample equalizing to be the same as the moisture of ambient air and no condensation occurs on the tube walls.

This prior art solution involves the following drawbacks. The tube material is only capable of a limited transfer of water through the wall per unit time, whereby the water splashed from the tubing of a respiration apparatus, a patient's mucus or blood may end up on a measuring sensor. Dust in the air also finds its way to a measuring sensor and causes problems there.

In order to overcome the problems described above a special type water separator has been developed. Said known water separator is described in U.S. Pat. No. 4,886,528.

The device shown in U.S. Pat. No. 4,886,528 operates quite satisfactorily when placed in its normal upright position. When however said device is not in upright position the performance was hindered as soon as some water blocked the filter area leading to the side flow. When the filter area is blocked, the vacuum needed to force mucus and other liquids to a container cannot be obtained.

BRIEF DESCRIPTION OF THE INVENTION

The object of the present invention is to provide a water separator by means of which the drawbacks of the prior art technique can be eliminated. This has been achieved by means of a water separator of the invention. The invention is characterized in that at least a part of the third chamber is formed to extend over essentially about 360 degrees around a cross sectional area of the housing.

An advantage of the invention is that the device is practically position independent, i.e. the flow by which harmful mucus and other liquids are forced to the container is in any practical positions of the device never totally blocked. Another advantage of the invention is its simplicity whereby the invention can be taken into use and also used with considerably low costs.

BRIEF DESCRIPTION OF THE DRAWINGS

In the following, the invention will be described in more detail by means of the attached drawing in which.

DETAILED DESCRIPTION OF THE INVENTION

Figure 1:
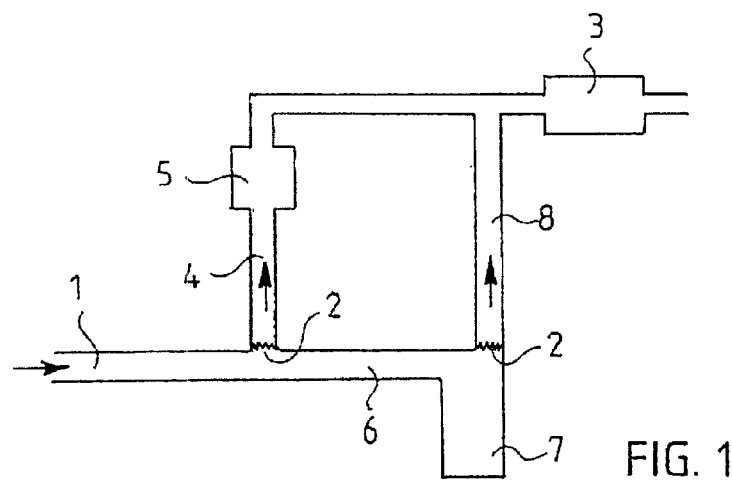
FIG. 1 shows the basic principle of a water separator.

FIG. 1 shows the basic principle of a water separator. A gas sample is brought from a patient via a conduit 1. The gas sample is divided into two partial flows by using a hydrophobic filter 2. The first flow portion is sucked by means of a pump 3 through the filter 2 into a conduit 4 to a measuring sensor 5. The second flow portion is sucked by means of a pump through a conduit 6 into a water receiving means 7. The water receiving means 7 is connected to the pump 3 by a conduit 8, which is also provided with a hydrophobic filter 2 which prevents liquid flow from the water receiving means 7 through the conduit 8, i.e. the discharge means, to the pump 3.

Figure 2:
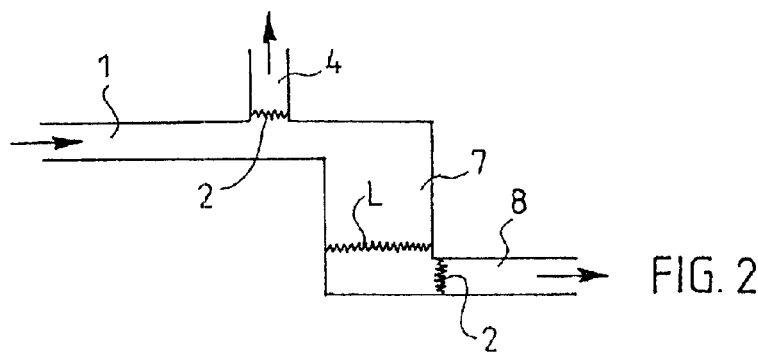
FIG. 2 shows the basic problem of the water separator.

In this connection it is important to realize that the gas sample from a patient may contain mucus and other liquids which may block the hydrophobic filter in the conduit 4 leading to the sensor 5. When the flow to the sensor 5 is blocked then a flow through the conduit 8 and 6, i.e. the cleaning flow builds a vacuum which forces mucus and other liquids to the water receiving means 7, and therefore the flow through the conduit 4 to the sensor 5 is no more blocked. To make this system position independent the cleaning flow, ie. the flow through conduit 8, must never be totally blocked. If the cleaning flow always has access to the water receiving means through hydrophobic filter then the flow will be able to build a vacuum sufficient to clean the path between the patient circuit and the sensor. FIG. 2 shows the problem discussed above, ie. how the flow to the sensor can be blocked if the separator is tilted. The level of mucus and other liquids is shown with a reference L.

The principle described above is already described in U.S. Pat. No. 4,886,528, and therefore the details of said known principle is not described more thoroughly in this connection.

Figure 3:
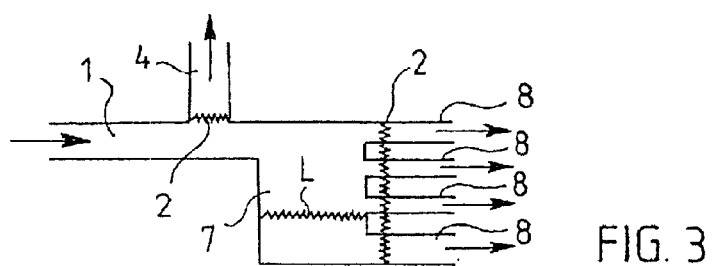
FIG. 3 shows the principle of the solution of the problem shown in FIG. 2.

FIG. 3 shows a principle of the solution of the problem shown in FIG. 2. FIG. 3 shows that the cleaning flow is not blocked in spite of the fact that the device is tilted. This principle operates quite well in most common circumstances but cannot be used in extreme conditions.

Figure 4:
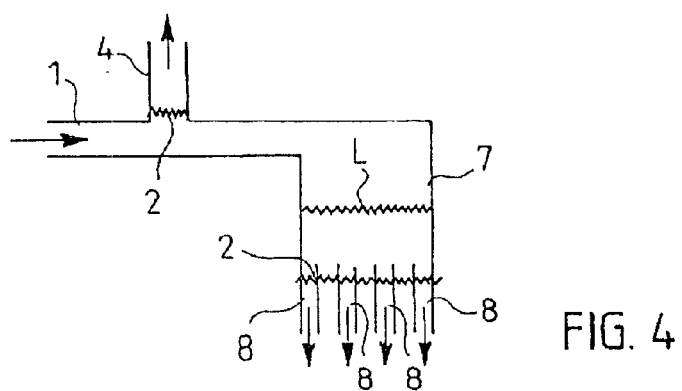
FIG. 4 shows the problem still existing if the principle shown in FIG. 3 is used.

FIG. 4 shows a problem still existing if the principle shown in FIG. 3 is used. In FIG. 4 the device is tilted upside down which leads to the fact that the cleaning flow is blocked.

Figure 5:
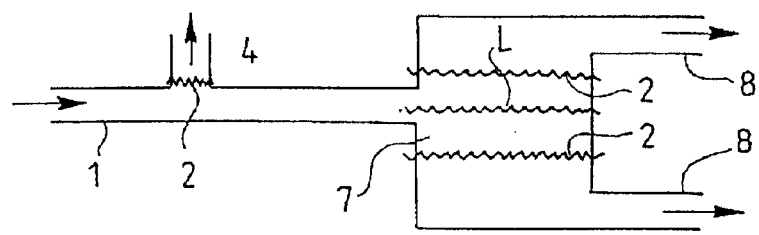
FIG. 5 shows the solution of the problem shown in FIG. 4.
Figure 6:
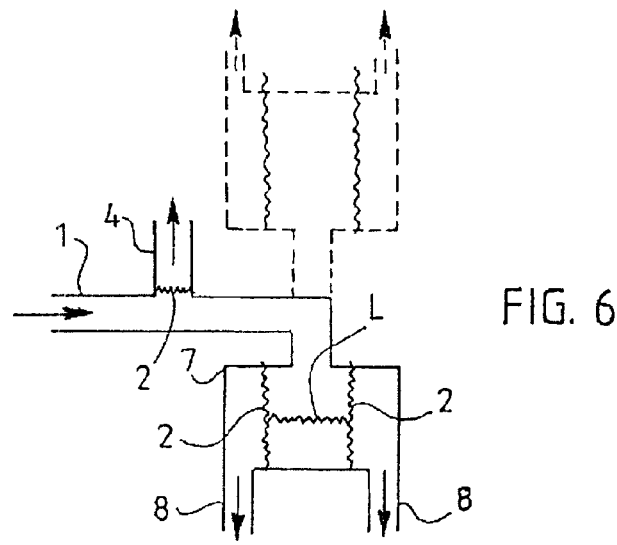
FIG. 6 shows how the solution described in FIG. 5 works in different positions.

FIGS. 5 and 6 show principles how the problem shown in FIG. 4 can be solved, ie. FIGS. 5 and 6 show the principle to make a completely position independent water separator. FIG. 6 shows the device in two positions. The position shown by phantom lines is a normal operating position and the position shown by solid lines is an upside-down position. FIGS. 5 and 6 show that the cleaning flow from the water receiving means 7 through conduit 8 is never totally blocked, and therefore the vacuum needed to force mucus and other liquids from conduit 1 to the water receiving means 7 is always created.

FIGS. 7–11 show one practical embodiment of the invention. This embodiment uses the principle shown in FIG. 3. In FIGS. 7–11 same reference numbers are used as in FIGS. 1–4 in connection with corresponding details.

Figure 7:
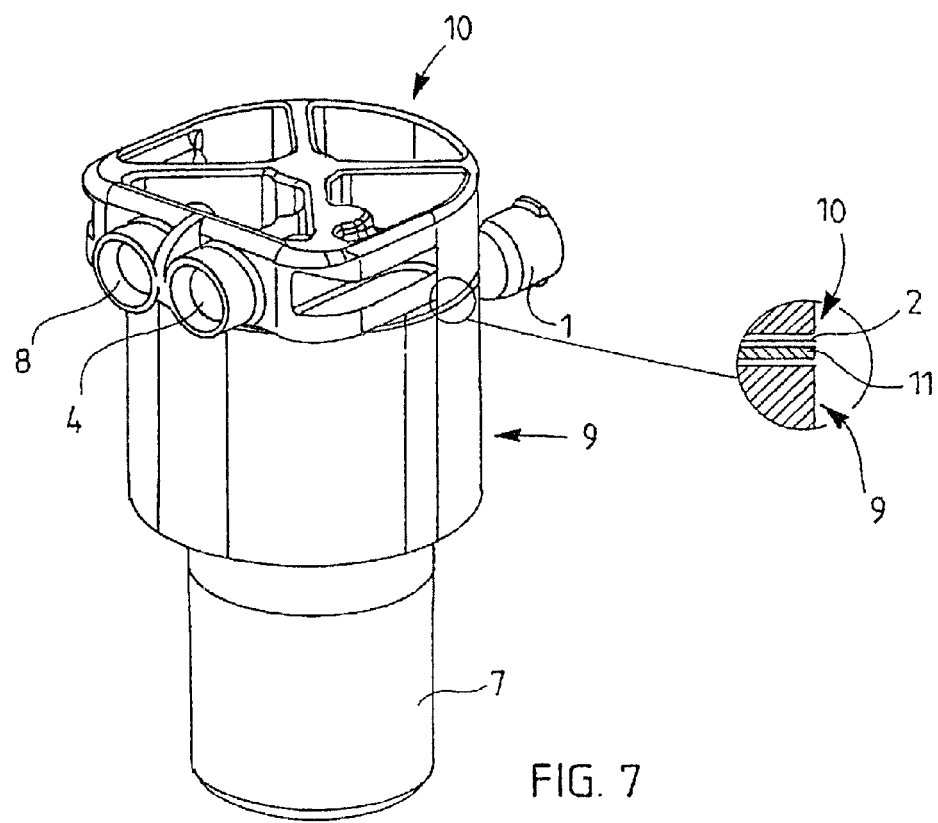
FIG. 7 shows a water separator according to one embodiment of the invention.
Figure 8:
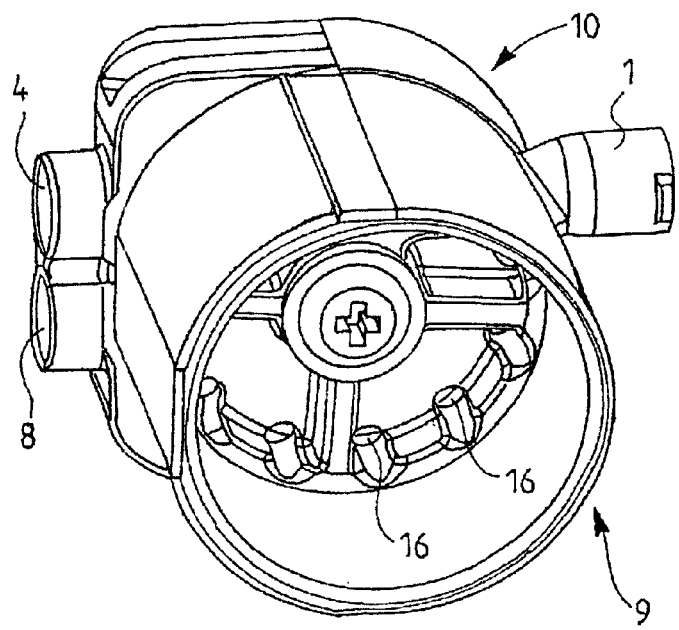
FIG. 8 shows the water separator of FIG. 7 seen from below and without water receiving means.

FIG. 7 shows a housing which consists of a lower part 9 and an upper part 10 which are mounted gas-tightly against each other. Between the lower part 9 and the upper part 10 there are a gasket 11 and also a hydrophobic filter 2. Hydrophobic filter 2 forms a gas permeable and liquid impermeable wall as described later. The material used for said filter 2 can be for instance 100% expanded Polytetrafluorethylene, ie. the filter 2 can be a membrane having thickness of 0.2 mm. Said filter is shown in connection with figure 7.

In the embodiment of FIGS. 7–11 the boundary surfaces of the lower part 9 and the upper part 10 are provided with grooves 12, 13 and 14. Said grooves together with the hydrophobic filter 2 form chambers by which the flow connections between conduit 1 from the patient and conduit 4 to the sensor 5, and between conduit 1 and conduit 8 respectively are formed.

The first chamber is formed by groove 12 and first wall 2, ie. filter, and the second chamber is formed by groove 13 and said first wall 2. Filter 2 forming said first wall is of gas permeable and liquid impermeable material separating said chambers from each other, whereby a first portion of gas from the gas sample from the patient passes through the filter 2 from the first chamber to the second chamber, and flows further to the sensor 5. A second portion of the gas and liquid remaining in the first chamber flows along the first chamber as shown in FIG. 5 by arrows through a conduit 15 to the water receiving means 7 where liquid is separated from the gas.

According to the basic principle of the invention the water separator comprises a third chamber which is formed so that at least a part of said third chamber extends essentially over about 360 degrees around a cross sectional area of the housing. This means that the third chamber is formed and placed so that at least a part of said chamber extends over wide area of the cross sectional area of the housing. Said chamber or a part of it can for instance be placed so that it is pretty near to the outer walls of the housing when looking the horizontal cross section of the housing. In the embodiment of FIGS. 7–11 said third chamber is formed of several channels 16 placed with a distance to each other. As seen from the figures said channels 16 are placed so that they are pretty near to the outer walls of the housing and therefore extend around the cross sectional area of the housing. Said construction is clearly shown in FIGS. 8, 9 and 10. In this connection it is however important to realize that the embodiment shown is not the only one possible. It is for instance quite possible to place the channels 16 so that they lie nearer to or eccentrically in respect to the center of the housing etc.

Figure 11:
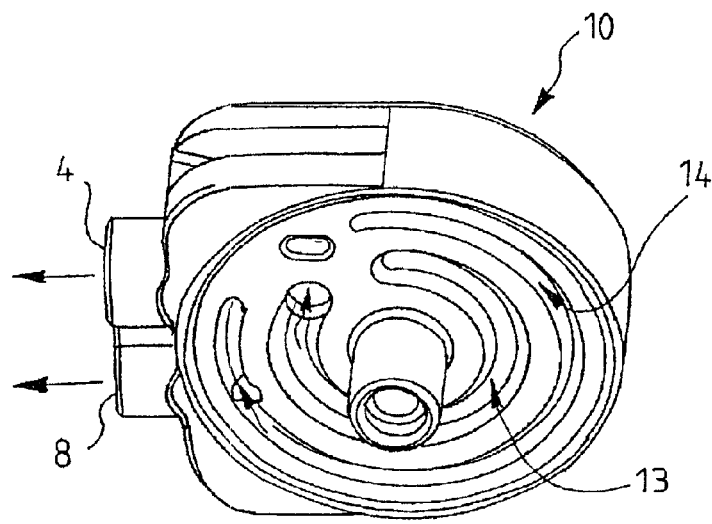
FIG. 11 shows the upper part of the housing used in the embodiment of FIG. 7.

Said third chamber is in connection with fourth chamber through second wall which is formed by gas permeable and liquid impermeable filter 2, ie. said second wall separates the third and fourth chamber from each other in the same way as told earlier in connection with the first and second chambers. In the embodiment of FIGS. 7–11 the fourth chamber is formed by a groove 14, said detail is shown in FIG. 11. The filter 2 prevents liquid flow from the water receiving means 7 to the pump 3 through conduit 8. The filter 2 is in this embodiment a flat piece of material forming separation walls of the first and second, and third and fourth chamber, respectively. The pump 3 creates vacuum which forces liquid and eventual mucus etc. from the first chamber to the water receiving means 7.

The gist of the present invention is that the third chamber is formed so that the flow path, ie. the cleaning flow path, from the water receiving means to the pump through filter is always open in any practical positions of the water separation device, and therefore vacuum needed for forcing mucus etc. from the first chamber to the water receiving means can be created in any practical circumstances. In other words by using the invention the flow to the pump is open in most of the practical situations, and therefore the flow will be able to build a vacuum sufficient to clean the path between the patient circuit and the sensor.

Figure 9:
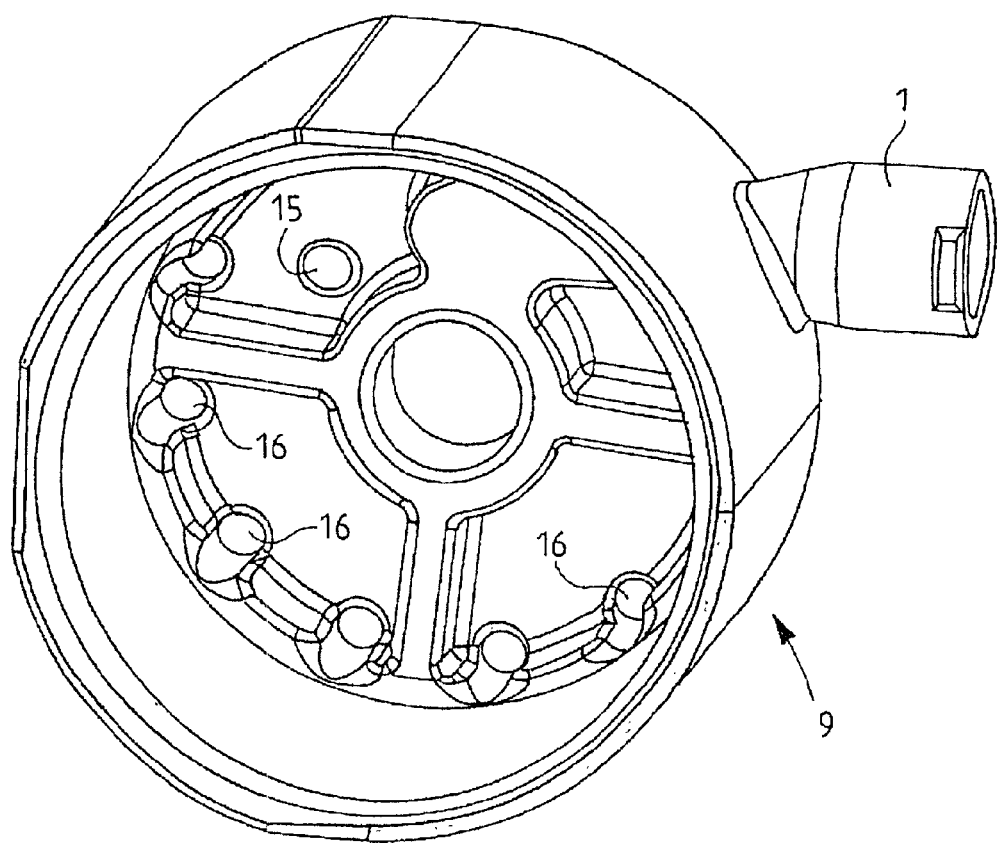
FIGS. 9 and 10 show the lower part of the housing used in the embodiment of FIG. 7.
Figure 10:
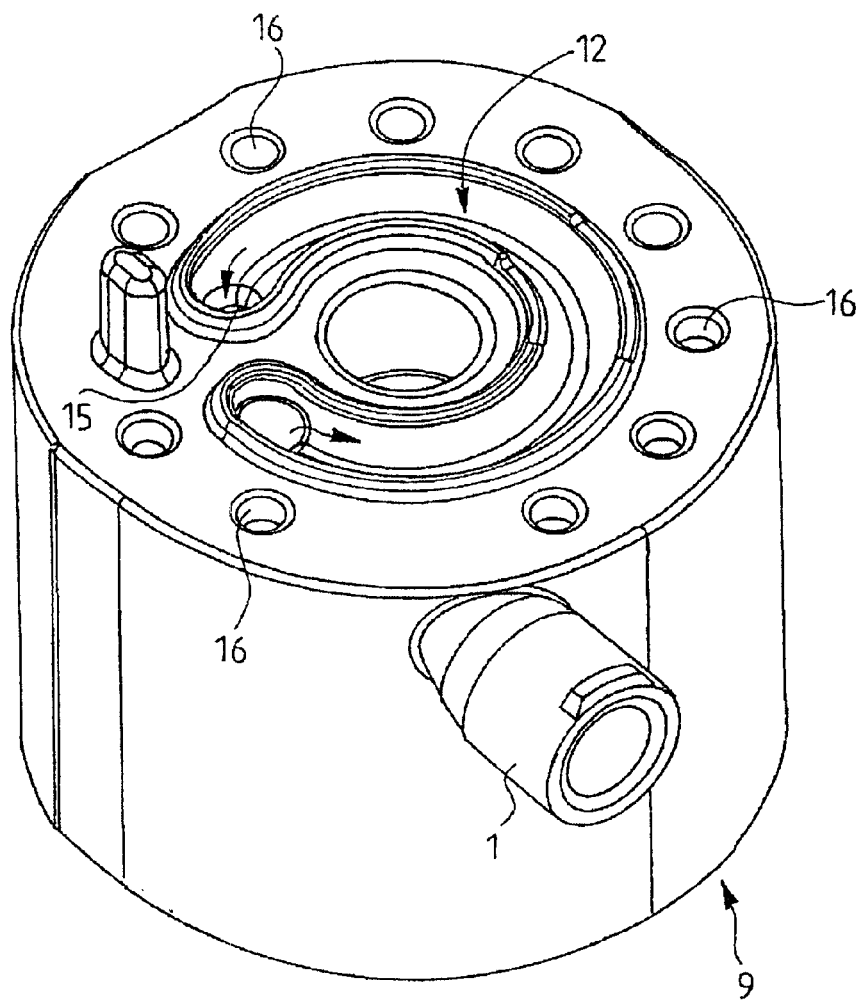

The embodiment described above is not the only one but within the spirit of the invention it is quite possible to make the third chamber by for instance combining the channels 16 into one and single curved channel extending over essentially about 360 degrees around the cross sectional area of the housing. Said curved channel which is in flow connection with the fourth chamber through filter 2, can be connected to the water receiving means 7 for instance by one channel or alternatively by several channels, ie. for instance by using channels as shown in FIG. 9.

Figure 12:
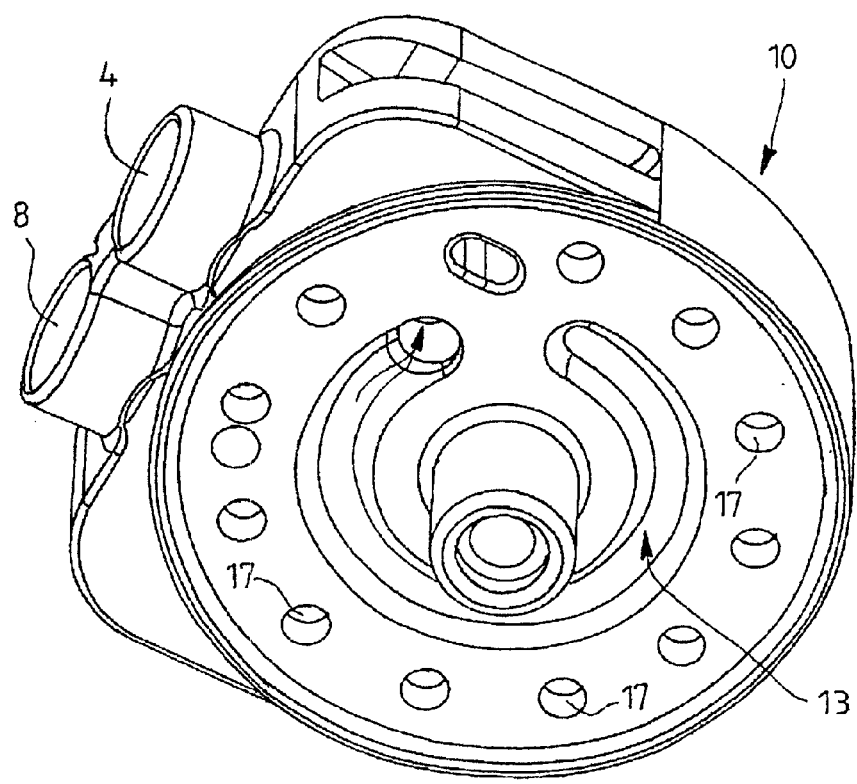
FIG. 12 shows an alternative embodiment of the upper part of the housing.

It is also quite possible to form the fourth chamber in the same way as the third chamber in the embodiment of FIGS. 7–11, ie. by making several channels 17 and placing said channels 17 into alignment with the channels 16 forming the third chamber. Channels 17 are naturally combined in the upper part 10 of the housing so that there is a flow connection into conduit 8. This embodiment is shown in FIG. 12. Channels 17 can also naturally be used in combination with a third chamber formed by a curved channel.

The channels, for instance channels 16 need not be parallel to the main line of the water separator, for instance the symmetry line in the embodiment of FIG. 7, but said channels can also be in angled position in respect to said main line. The position of the channels may vary according to forms and sizes of the housing and the water receiving means.

Figure 13:
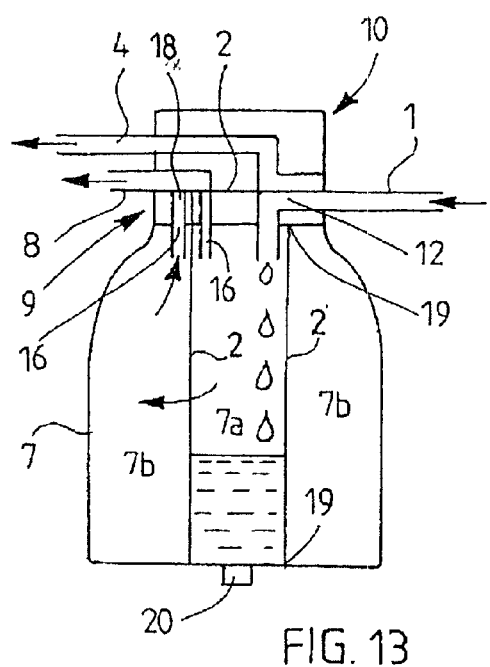
FIGS. 13 and 14 show the operating principle of the second alternative embodiment of the present invention.
Figure 14:
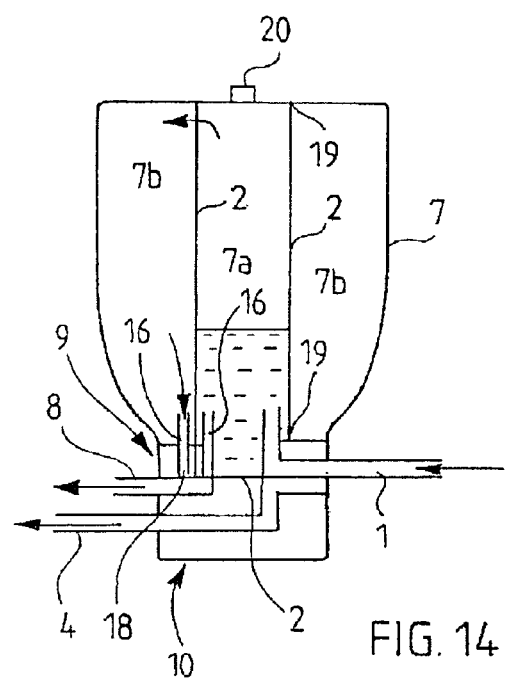

In order to improve the position independent feature it has been found advantageous to make a slightly modified version of the basic embodiment of the invention shown in FIGS. 7–11. Said improvement is obtained by using the principle shown in FIGS. 5 and 6. The operating principle of said modified embodiment is shown in detail in FIGS. 13 and 14. In FIGS. 13 and 14 the same reference numbers are used in corresponding details as earlier in connection with FIGS. 1–12.

In the embodiment of FIGS. 13 and 14 the second wall 2 is arranged to extend from the housing 9,10 to the bottom part of the water receiving means 7 so that the second wall 2 divides the water receiving means 7 into two spaces 7a and 7b. The material of the second wall in FIGS. 13 and 14 can be for instance the same as mentioned earlier in connection with the earlier embodiments. In the embodiment of FIGS. 13 and 14 the second wall 2 forms the part of the third chamber extending essentially about 360 degrees around the cross sectional area of the housing. The first chamber 12, 2 is in flow connection with one space 7a and the other space 7b is in flow connection through channel 16 with the discharge means 8. The second wall can be for instance a tubular form wall which is connected with air tight connection 19 to the housing and to the bottom part of the water receiving means 7. Said air tight connection can be made for instance by glueing, welding, insert molding etc. Said tubular wall need not extend to the bottom part of the water receiving means 7 as shown in FIGS. 13 and 14. Said tubular wall can also be a cup-like structure extending from the housing towards the bottom part of the water receiving means.

In the embodiment described above and in FIGS. 13 and 14 it is further advantageous optionally to use a third wall 18 formed of a gas permeable and liquid impermeable material. Said material can be for instance 100% expanded Polytetrafluoroethylene. Said third wall can very advantageously be formed as an integral part with the filter or wall discussed earlier in connection with FIG. 7. Said third wall 18 is however only an optional arrangement in the embodiment of FIGS. 13 and 14 because the water separator shown in FIGS. 13 and 14 operates quite well with a tubular second wall 2 only.

The operating principle of the embodiment is shown in FIGS. 13 and 14, ie. there is always, ie. in every position of the water separator a flow connection from the space 7a for the gas through the second wall 2 to the space 7b and further to the conduit 8 and still further to the pump 3. Water stays in the space 7a and cannot flow into space 7b because of the second wall 2, but gases flow through the second wall 2 as shown by the arrows in FIGS. 13 and 14, and therefore there is always in any position of the device a flow connection for gas from the space 7b through channels 16. Owing to said fact the pump is always able to create a vacuum sufficient to clean the path between the patient circuit connected to conduit 1 and the sensor 5.

In order to improve the vacuum effect it is advantageous to form the device so that there is flow connection to the pump creating vacuum from both of the spaces 7b and 7a. Said arrangement is shown in FIGS. 13 and 14 in which one channel or some channels 16 are arranged to be in flow connection with the space 7a instead of the space 7b. The flow connection from the space 7a to the pump is created through wall 2 arranged between the lower part 9 and the upper part as shown in FIGS. 13 and 14. Said channels are inoperable if the device is upside down (FIG. 14) but improves the vacuum effect in the normal operating position of the device (FIG. 13). The channels 16 which are in flow connection with the space 7b are operable in any position of the device and therefore this embodiment is completely position independent.

The water from the space 7a can be removed by any suitable way, for instance by using a draining device 20 mounted in the bottom part of the water receiving means 7.

Figure 18:
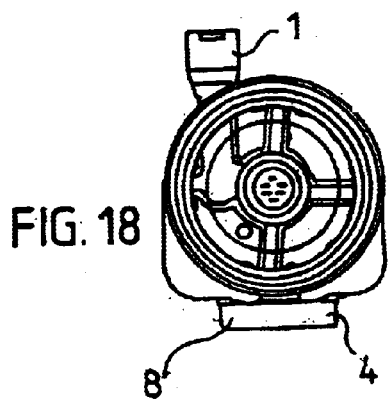
FIGS. 15–18 show an example of the actual device using the operating principle of FIGS. 13 and 14.
Figure 17:
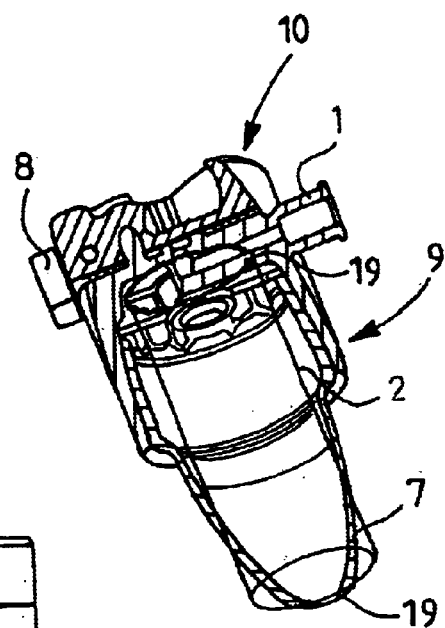
Figure 15:
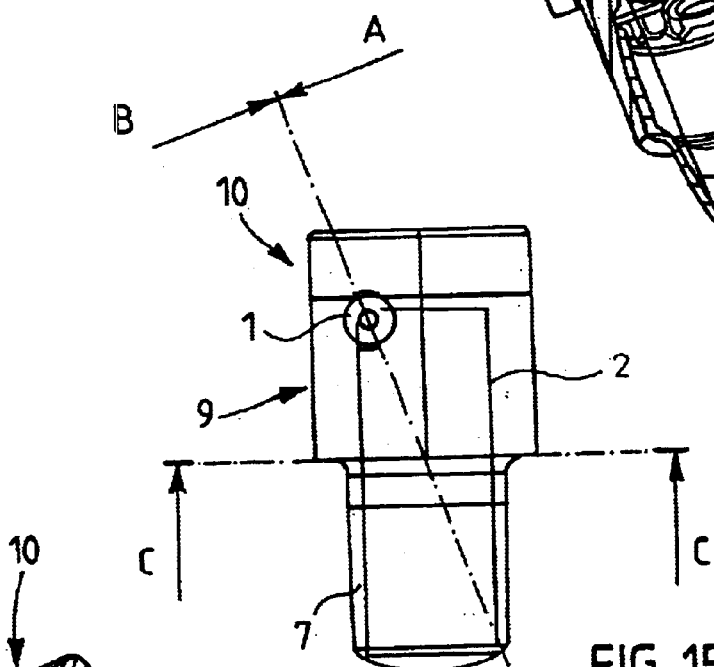
Figure 16:
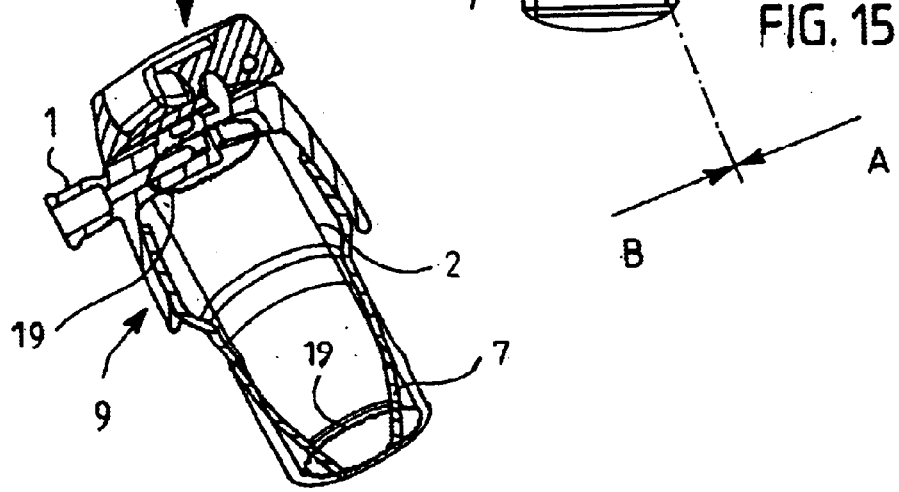

FIGS. 15–18 show an example of the actual device using the principle shown in FIGS. 13 and 14. FIG. 16 is a view according to arrows A—A in FIG. 15. FIG. 17 is a view according to arrows B—B in FIG. 15. FIG. 18 is a view according to arrows C—C in FIG. 15.

The embodiments described above are by no means intended to restrict the invention, but the invention can be modified quite freely within the scope of the claims. It is thus clear that the invention or its details do not absolutely need to be just like shown in the figures, but solutions of other kinds are also possible. For instance the walls formed of gas permeable and liquid impermeable material separating the chambers, i.e. the filters, need not be formed by using a flat piece of material but said walls can be materialized also by using for instance the teachings of U.S. Pat. No. 4,886,528, i.e. by using tubular constructions etc.

What is claimed is:

1. A water separator for a gas analyzer, comprising a housing, a first chamber disposed within the housing, a second chamber disposed within the housing, a first wall formed of a gas permeable and liquid impermeable material separating the chambers, means for introducing a gas sample containing a liquid into the first chamber with a first portion of gas passing through the first wall to the second chamber and a second portion of the gas and the liquid remaining in the first chamber, means for flowing said first portion of the gas from the second chamber to a measuring unit, a water receiving means mounted in the housing, and connected to the first chamber for receiving the second portion of the gas and for separating liquid from the second portion of the gas, a third chamber connected to the water receiving means, a fourth chamber, a second wall formed of a gas permeable and liquid impermeable material separating the third and fourth chambers, the second portion of the gas passing through the second wall to the fourth chamber, and discharge means for discharging the second portion of the gas from the fourth chamber and connecting the water receiving means with a source of vacuum, at least a part of the third chamber being formed to extend over essentially about 360 degrees around a cross sectional area of the housing.

2. The water separator according to claim 1, wherein the third chamber is formed of several channels placed with a distance to each other.

3. The water separator according to claim 2, wherein the third chamber is formed of at least three channels.

4. The water separator according to claim 1, wherein the third chamber is formed of a curved channel connected by at least one channel to the water receiving means.

5. The water separator according to claim 1, wherein the second wall is arranged to extend from the housing towards the bottom part of the water receiving means dividing the water receiving means into two spaces and forming the part of the third chamber extending essentially about 360 degrees around the cross sectional area of the housing, and that the first chamber is in flow connection with one space and at least the other space is in flow connection with the discharge means.

6. The water separator according to claim 5, wherein the other space is in flow connection with the discharge means through a third wall formed of a gas permeable and liquid impermeable material.

7. The water separator according to claim 1, wherein the fourth chamber is arranged to form a curved passage extending around the cross section area of the housing and the third chamber being arranged to open at the area of curved passage essentially over the entire length of the curved passage.

8. The water separator according to claim 2, wherein the fourth chamber is formed of several channels placed in alignment with the channels forming the third chamber.

9. The water separator according to claim 5, wherein the second wall is a tubular form wall.

10. The water separator according to claim 9, wherein the second wall is connected with air tight connection to the housing and to the bottom part of the water receiving means.

11. The water separator according to claim 5, wherein both of the spaces formed by the second wall in the water receiving means are in flow connection with the discharge means.

12. The water separator according to claim 2, wherein the second wall is arranged to extend from the housing towards the bottom part of the water receiving means dividing the water receiving means into two spaces and forming the part of the third chamber extending essentially about 360 degrees around the cross sectional area of the housing, and that the first chamber is in flow connection with one space and at least the other space is in flow connection with the discharge means.

13. The water separator according to claim 3, wherein the second wall is arranged to extend from the housing towards the bottom part of the water receiving means dividing the water receiving means into two spaces and forming the part of the third chamber extending essentially about 360 degrees around the cross sectional area of the housing, and that the first chamber is in flow connection with one space and at least the other space is in flow connection with the discharge means.

14. The water separator according to claim 4, wherein the second wall is arranged to extend the housing towards the bottom part of the water receiving means dividing the water receiving means into two spaces and forming the part of the third chamber extending essentially about 360 degrees around the cross sectional area of the housing, and that the first chamber is in flow connection with one space and at least the other space is in flow connection with the discharge means.

15. The water separator according to claim 2, wherein the fourth chamber is arranged to form a curved passage extending around the cross section area of the housing and the third chamber being arranged to open at the area of curved passage essentially over the entire length of the curved passage.

16. The water separator according to claim 3, wherein the fourth chamber is arranged to form a curved passage extending around the cross section area of the housing and the third chamber being arranged to open at the area of curved passage essentially over the entire length of the curved passage.

17. The water separator according to claim 4, wherein the fourth chamber is arranged to form a curved passage extending around the cross section area of the housing and the third chamber being arranged to open at the area of curved passage essentially over the entire length of the curved passage.

18. The water separator according to claim 3, wherein the fourth chamber is formed of several channels placed in alignment with the channels forming the third chamber.

19. The water separator according to claim 6, wherein the second wall is a tubular form wall.

20. The water separator according to claim 6, wherein both of the spaces formed by the second wall in the water receiving means are in flow connection with the discharge means.

* * * * *